United States Patent [19]

Young

[11] Patent Number: 4,863,506
[45] Date of Patent: Sep. 5, 1989

[54] METHODS FOR REGULATING THE GROWTH OF PLANTS AND GROWTH REGULANT COMPOSITIONS

[75] Inventor: Donald C. Young, Fullerton, Calif.

[73] Assignee: Union Oil Company of California, Los Angeles, Calif.

[21] Appl. No.: 511,161

[22] Filed: Jul. 6, 1983

[51] Int. Cl.$^4$ ............................................. A01N 37/36
[52] U.S. Cl. ....................................... 71/113; 71/106; 71/76; 71/77
[58] Field of Search ................................ 71/113, 106

[56] References Cited

U.S. PATENT DOCUMENTS

| 2,535,875 | 12/1950 | Stewart . | |
|---|---|---|---|
| 3,172,816 | 3/1965 | Swintosky | 71/DIG. 2 |
| 3,712,804 | 1/1973 | Mueller et al. | 71/113 |
| 4,265,654 | 5/1981 | Takematsu et al. | 71/86 |
| 4,435,203 | 3/1984 | Funaki et al. | 71/76 |
| 4,813,997 | 3/1989 | Kennersley et al. | 71/66 |

FOREIGN PATENT DOCUMENTS

| 2200941 | 8/1982 | Fed. Rep. of Germany . |
| 157167 | 12/1975 | Japan . |
| 1561475 | 2/1980 | United Kingdom . |

OTHER PUBLICATIONS

Todorova et al., Chem. Abst., vol. 93 (1980) 68595y.
Tung et al., Chem. Abst., vol. 67 (1967) 89968a.
Chem. Abst., 8th Collective Subject Index, pp. 17196 and 17197.
Terent'e/ et al., Chem. Abst., vol. 66 (1967) 54601c.
Merck Index (1983) entry No. 5174.
Radler et al., Chem. Abst., vol. 74 (1971) 50803n.
Smith et al., Chem. Abst., vol. 73 (1970) 42673j.
Hummel, Chem. Abst., vol. 42 (1948) 4097e.

*Primary Examiner*—Catherine L. Mills
*Attorney, Agent, or Firm*—Michael H. Laird; G. Wirzbicki

[57] ABSTRACT

L-(d)-lactic acid, the dextrorotatory isomer of lactic acid, is an effective plant growth regulant which exhibits classical growth regulant activity at very low concentrations and dosage rates. It can be employed to beneficially stimulate the growth of all plant varieties and is particularly useful for stimulating the growth of commercial crops. As is the case with other growth regulants, L-lactic acid can also be employed to inhibit the growth of plants when applied at sufficiently high concentrations. Thus, L-lactic acid can be employed to stimulate the growth of desired plants, to stimulate the fruit production of fruit-bearing plants, and to inhibit the growth of undesired vegetation. Novel compositions which comprise mixtures of L-(d)-lactic acid and one or more preservatives which are sufficient to prevent the hydrolytic and/or bacterial decomposition of the active isomer are also disclosed.

33 Claims, 1 Drawing Sheet

METHODS FOR REGULATING THE GROWTH OF PLANTS AND GROWTH REGULANT COMPOSITIONS

BACKGROUND OF THE INVENTION

1. Field of the Invention

This invention relates to methods of regulating the growth of plants and, in particular, it relates to methods useful for stimulating the growth and/or fruit production of plants, to methods of inhibiting the growth of undesired vegetation, and to compositions useful for regulating plant growth.

2. Description of the Art

Plant growth regulants can be defined as compounds and/or preparations which, in minute amounts, alter the behavior of ornamental and/or crop plants and/or the produce of such plants through physiological (hormonal) rather than physical action. They may either accelerate or retard growth, prolong or break a dormant condition, promote rooting, fruit-set, or increase fruit size or quantity, or affect the growth and/or productivity of plants in other ways. Plant growth regulants are currently classified into one or more of six categories: auxins, gibberellins, cytokinins, ethylene generators, inhibitors, and retardants. Illustrative of known auxins are indole acetic acid, 24-D (2,4-dichlorophenoxyacetic acid), MCPA (4-chloro-2-methyl phenoxyacetic acid), MCPB (4-[(4-chloro-o-tolyl)oxy] butyric acid) which susceptible plants oxidize to MCPA, and BNOA (beta-napthoxy-acetic acid). Gibberellins include gibberellic acid and its derivatives, while cytokinins include compositions such as zeatin, kinentin, and benzyl anidene. Presently known ethylene generators include ethylene and Ethephon [(2-chloroethyl) phosphoric acid]. Presently known inhibitors include benezoic acid, gallic acid, and cinnamic acid, while retardants, a recently developed class of plant growth regulants, include compositions which are especially useful in plant height control, particularly in commercial greenhouse-grown floricultural crops.

Lactic acid (alpha-hydroxypropionic acid) is well known and is widely employed in industry as a chemical intermediate. It is usually present in the form of the racemic mixture which is an equal molar mixture of the two possible optical isomers of alpha-hydroxypropionic acid— the levorotatory and dextrorotatory isomers. Levorotatory (l) isomers are isomers of an optically active compound which rotate a beam of polarized light to the left; the dextrorotatory (d) isomers are isomers of the same compound which rotate a beam of polarized light to the right. A second convention employed to define the configurational relationships of dissimilar functional groups bonded to an asymmetric carbon atom the Fischer method, is based on the geometric arrangement of functional groups relative to each other rather than on the direction (left or right) in which a standard solution of the compound rotates a beam of polarized light. In accordance with the Fischer method, any compound which contains an asymmetric carbon atom of the same configuration as the asymmetric carbon in the arbitrary standard dextrorotatory glyceraldehyde is classified in the D series while compounds in which the asymmetric carbon atom has the opposite configuration are classified in the L series. Although the Fischer D and L classifications do not correlate with dextro- (d) and levorotatory (l) optical activity for all compounds, those classifications can be used in combination with the optical activity classifications d and l to define both the geometric arrangement and specific optical activity of any optically active isomer. Thus, the L-isomer of lactic acid, which is dextrorotatory, is defined as L-(d)-lactic acid, and the D isomer is defined as D-(l)-lactic acid. However, both of these characteristics of relatively simple compounds such as lactic acid can be adequately defined by reference to only one classification system. L-lactic acid is known to be dextrorotatory and l-lactic acid is known to have the D configuration according to Fischer. For this reason, the D and L isomers of lactic acid are usually identified only by the D and L designations and without explicit reference to their optical activity. The Fischer classification method is well known in the art and is discussed in more detail in "Introduction to Organic Chemistry", Fieser and Fieser, D. C. Heath and Co., Boston, Mass., (1957) at pages 209–215.

Lactic acid is prevelant in a variety of synthetic and naturally occurring products such as dairy products and fermentation products in which it occurs primarily as the racemic mixture. Specialized fermentation processes can be employed to selectively manufacture either the levorotatory or dextrorotatory isomers. Although some commercially available agricultural products contain fermentation products and lactic acid and are marketed for various applications in the agricultural industry, it has not been observed or suggested that L-(d)-lactic acid is an active plant growth regulant. Furthermore, the lactic acid-containing compositions which are marketed in the agricultural industry usually contain the racemic mixture of both optical isomers in addition to cations such as sodium, potassium, ammonium, etc., and/or other compounds such as surfactants, pesticides, etc., which can react with L-lactic acid and destroy its growth regulant activity.

It has been suggested that alpha-hydroxy carboxylic acids of higher molecular weight than lactic acid exhibit specific growth regulant activity regardless of the configuration or optical activity of the carboxylic acid employed. U.S. Pat. No. 3,712,804, Mueller et al., discloses that certain alpha-substituted carboxylic acids increase the yield of certain crops by improving the ability of the plant to assimilate water from its environment. The acids have 7 to 10 carbon atom per molecule and the alpha carbon atoms is substituted with one or more functional groups including oxy, hydroxy, amine, and carboxyl groups. The acids are applied to very young plants and the salts and lower alkyl esters and amines have growth regulant activity similar to that of the free acid. The compositions can also contain wetting agents.

The plant growth regulants referred to above and otherwise known in the art, including those discussed in U.S. Pat. No. 3,712,804, all suffer from certain disadvantages that make their use, at least in some applications, less desirable than would be the use of L-lactic acid. Many growth regulant compositions, particularly those which exhibit herbicidal activity at higher dosage rates, are toxic to plants, the environment, and/or animals, including humans. Many are not readily available and are relatively expensive to manufacture as compared to L-lactic acid. Also, many of the known growth regulants such as the alpha-functional carboxylic acids, salts, esters and amines discussed in U.S. Pat. No. 3,712,804, require plant treatment at a time that may not be opportune for the grower in all instances. Furthermore, many known regulants exhibit a limited spectrum of growth regulant activity, are not useful with many plant varieties, and/or do not adequately regulate crop productivity.

Accordingly, a need exists for improved methods for regulating the growth of plants and for improved compositions useful in such methods. In particular, a need exists for improved methods and compositions for stimulating the desired growth of plants, inhibiting the growth of undesired vegetation, reducing the toxic effects of such methods and compositions on the environment and animals, including humans, and reducing the expense of so regulating plant growth.

It is therefore a principal object of this invention to provide novel methods for regulating the growth of plants.

Another object of this invention is the provision of novel plant growth regulant compositions.

Yet another object of this invention is the provision of methods and compositions for stimulating the growth and productivity of agricultural and ornamental plants.

Yet another object is the provision of improved methods and compositions for inhibiting the growth of undesired vegetation.

Another object of this invention is the provision of plant growth regulant compositions which are nontoxic to animals and to the environment.

Another object of this invention is the provision of relatively inexpensive methods for regulating the growth of plants which do not require exposure of applicators, other personnel, or the environment to either toxic or corrosive materials.

Other objects, aspects and advantages of this invention will be apparent to one skilled in the art in view of the following disclosure, the drawings, and the appended claims.

SUMMARY OF THE INVENTION

Briefly, the invention provides novel methods for regulating the growth of plants and compositions useful in such methods. The methods of this invention involve regulating the growth of plants by contacting the plants with a growth regulating amount of a composition which contains the dextrorotatory L-(d)-isomer of lactic acid. The L-lactic acid preferably constitutes at least a major portion of the lactic acid present in the applied composition. These methods can be employed either to stimulate the growth and/or fruit production of crop plants and ornamental plants or to inhibit the growth of undesired vegetation.

The novel compositons of this invention exhibit plant growth regulant activity and contain lactic acid of which at least a major portion is the L-(d)-isomer of lactic acid. These compositions also contain a nonreactive preservative such as a sufficient amount of acid to maintain the pH of the composition within the range of about 5 or less and/or a sterilant which is sufficient to inhibit the bacterial decomposition of the lactic acid.

The methods of this invention which employ relatively low concentrations and dosage rates of the growth-active L-isomer of lactic acid are useful for increasing the growth and/or fruit production of essentially all plant varieties. On fruiting plants, the methods of this invention can be employed to increase both the size and quantity of the fruit produced. These methods also hasten maturity of fruit thereby shortening the crop cycle and they increase the growth rate of agricultural and ornamental grasses, such as alfalfa, rye grass, etc. They can be employed to delay the senescence and thereby extend the fruiting period of annual fruit plants such as tomatoes and corn and to extend the fruiting period of perennials such as citrus, grapes, etc. These methods have the further advantage that they are nontoxic to the environment and to animals, and, at levels employed for stimulating plant growth, the compositions useful in the methods of this invention are nontoxic to the treated plants or to the harvested component of fruiting plants such as food products. Furthermore, the compositions useful in the methods of this invention are noncorrosive to storage, transport and application equipment and to animal and vegetable tissue. Thus, they can be easily and safely handled without damage to equipment, personnel, the crop, or the environment. The active component of the compositions useful in the methods of this invention—L-lactic acid—is readily available commercially and is relatively inexpensive, particularly in comparison to various other plant growth regulants which are expensive, sophisticated chemical compounds which require relatively sophisticated processes for their manufacture.

By the use of higher dosage rates of the L-lactic acid component, the methods of this invention can be employed to inhibit the growth of undesired vegetation without the disadvantages attendant to the use of various other herbicidal growth regulants such as toxicity to the environment and animals and corrosivity toward application, storage or shipping equipment and personnel.

All of the benefits associated with the use of the methods of this invention discussed above also result from the use of the novel compositons of this invention in such methods, whether those novel compositions are employed to stimulate or to inhibit vegetative growth.

BRIEF DESCRIPTION OF THE DRAWINGS

The methods and compositions of this invention will be better understood by reference to the drawings of which.

DETAILED DESCRIPTION OF THE INVENTION

Figure 1:
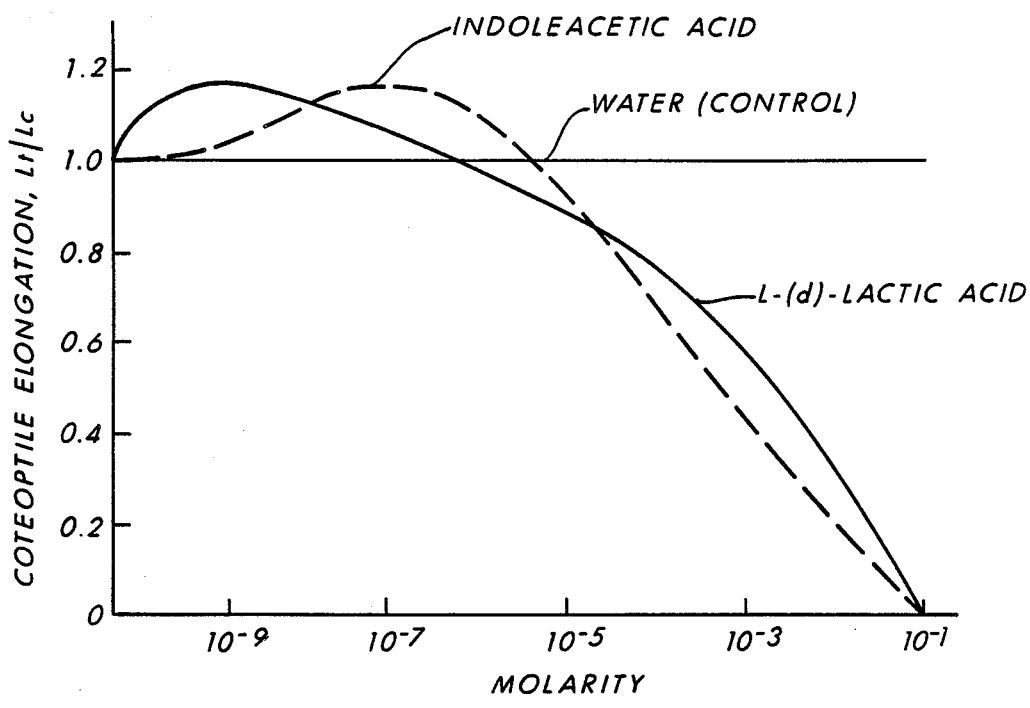
FIG. 1 is a graphic presentation of Cress Test results illustrating the root growth stimulating and inhibiting activity of L-lactic acid and of indoleacetic acid.

This invention provides novel methods for regulating the growth of plants and novel growth regulant compositions useful in such methods. The methods of this invention involve either stimulating or retarding the growth of plants (depending upon the dosage rate of the growth regulating composition employed) by contacting the plants with a composition comprising the dextrorotatory isomer of lactic acid. The novel compositions of this invention comprise lactic acid of which at least a major portion is the L-(d)-isomer of lactic acid and a preservative which is nonreactive with the lactic acid and which is sufficient to reduce or prevent the hydrolytic and/or bacterial decomposition of the lactic acid. The methods of this invention can be employed to increase vegetative growth and to increase the fruit production of fruit-producing plants. They can also be employed to hasten the maturity of plant fruit, delay the senescence (and thereby extend the fruiting period) of annual plants, and to extend the fruiting period of perennial plants.

The compositions useful in the methods of this invention are broad spectrum plant growth regulants; thus they can be employed to stimulate the growth and/or fruit-producing capacity or to inhibit the growth of all plant varieties, including fruiting and principally vegetative plants. Fruiting plants, for the purposes of this invention, include plants that bear any variety of produce other than vegetative growth such as annual and perennial vegetables, fruits, nuts, grains, fiber crops, and the flowering plants. Plants grown primarily for their vegetative productivity (the principal illustration being the wide variety of grasses grown for animal feeds and decorative purposes) can also be treated in accordance with the methods of this invention. Thus, the methods of this invention can be employed to stimulate the growth and fruit-bearing capacity (where relevant) of vegetables, fruits, nuts, grains, grasses, fiber crops, wood crops, and flowering plants.

All varieties of vegetables can be treated in accordance with these methods including lettuce, broccoli, asparagus, onions, tuberous crops such as potatoes, sugar beets and peanuts, tomatoes, beans, etc. Illustrative of fruits that can be treated in accordance with the methods of this invention are peaches, apples, citrus, avocados, cherries, grapes (varietal and table), bananas, etc. Treatable nut crops include walnuts, pecans, almonds, cashews, etc. Essentially all grains can be treated including corn, wheat, sorghum, maize, rice, barley, oats, etc. Illustrative grasses include alfalfa, bermuda, rye, and bluegrass, while illustrative fiber crops include cotton and flax. All wood crops can be stimulated by the methods of this invention including both hardwoods and conifers, such as oak, elm, maple, walnut, spruce, hemlock, alder, loblolly pine, redwood, mahogany, cypress, cedar, Douglas fir, and white pine. Flowering plants which can be treated in accordance with the methods of this invention include all varieties of domestic and commercially grown flowers, such as orchids, roses, chrysanthemums, azaleas, camellias, carnations, pansies, snapdragons, etc.

All plant varieties, including all of the annual and perennial, fruiting and vegetative plants referred to above can be inhibited and eliminated by the methods of this invention. However, it is usually preferable to inhibit the growth only of undesired vegetation such as weeds, brush and grasses that occupy vacant land and which can infiltrate commercial crops and domestic plantings. Illustrative of vegetation which is usually desirable to inhibit or eliminate are black mustard (*Brassica nigra*), curly dock (*Rumex crispus*), common groundsel (*Senecio vulgaris*), pineapple weed (*Matricaria matricarioides*), swamp smartweed (kelp) (*Polygonum coccineum*), prickly lettuce (*Lactuca scariola*), lance-leaved groundcherry (*Physalis lanceifolia*), annual sowthistle (*Sonchus oleraceus*), london rocket (*Sisymbrium irio*), common fiddleneck (*Amsinckia intermedia*), hairy nightshade (*Solanum sarrachoides*), shepherd's purse (*Capsella bursa-pastoris*), sunflower (*Helianthus annuus*), common knotweed (*Polygonum aviculare*), green amaranth (*Amaranthus hybridus*), mare's tail (*Conyza canadensis*), henbit (*Lamium amplexicaule*), cocklebur (*Xanthium strumarium*), cheeseweed (*Malva parviflora*), lambsquarters (*Chenopodium album*), puncture vine (*Tribulus terrestris*), common purslane (*Portulaca oleracea*), prostrate spurge (*Euphorbia supina*), telegraph plant (*Heterotheca grandiflora*), carpetweed (*Mollugo verticillate*), yellow starthistle (*Centaurea solstitialis*), milk thistle (*Silybum marianum*), mayweed (*Anthemis cotula*), burning nettle (*Urtica urens*), fathen (*Atriplex patula*), chickweed (*Stellaria media*), scarlet pimpernel (*Anagallis arvensis*), redroot pigweed (*Amaranthus retroflexus*), minnerslettuce (*Montia perfoliata*), turkey mullein (*Eremocarpus setigerus*), nettleleaf goosefoot (*Chenopodium murale*), prostrate pigweed (*Amaranthus blitoides*), silverleaf nightshade (*Solanum elaeagnifolium*), hoary cress (*Cardaria draba*), largeseed dodder (*Cuscuta indecora*), California burclover (*Medicago polymorpha*), horse purslane (*Trianthema portulacastrum*) field bindweed (*Convolvulus arvensis*), russian knapweed (*Centaurea repens*), flax-leaved fleabane (*Conyza bonariensis*), wild radish (*Raphanus sativus*), tumble pigweed (*Amaranthus albus*), stephanomeria (*Stephanomeria exigua*), wild turnip (*Brassica campestris*), buffalo goard (*Cucurbita foetidissima*), common mullein (*Verbascum thapsus*), dandelion (*Taraxacum officinale*), spanish thistle (*Xanthium spinosum*), chicory (*Cichorium intybus*), sweet anise (*Foeniculum vulgare*), annual yellow sweetclover (*Melilotus indical*), poison hemlock (*Conium maculatum*), broadleaf filaree (*Erodium botrys*), whitestem filaree (*Erodium moschatum*), redstem filaree (*Erodium cicutarium*), ivyleaf morning-glory (*Ipomea hederacea*), shortpod mustard (*Brassica geniculata*), buckhorn plantain (*Plantago lacenolata*), sticky chickweed (*Cerastium viscosum*), himalaya blackberry (*Rubus procerus*), purslane speedwell (*Veronica peregrina*), mexicantea (*Chenopodium ambrosioides*), spanish clover (*Lotus purshianus*), australian brassbuttons (*Cotula australia*), goldenrod (*Solidago californica*), citron (*Citrullus lanatus*), hedge mustard (*Sisymbrium orientale*), black nightshade (*Solanum nodiflorum*), chinese thornapple (*Datura ferox*), bristly oxtongue (*Picris echioides*), bull thistle (*Cirsium vulgare*), spiny sowthistle (*Sonchus asper*), tasmanian goosefoot (*Chenopodium pumilio*), goosefoot (*Chenopodium botrys*), wright groundcherry (*Physalis acutifolia*), tomatillo groundcherry (*Physalis philadelphica*), pretty spurge (*Euphorbia peplus*), bitter apple (*Cucumis myriocarpus*), indian tobacco (*Nicotiana bigelovii*), common morning-glory (*Ipomoea purpurea*), waterplantain (*Alisma triviale*), smartweed (*Polygonum lapathifolium*), mature sowthistle (*Sonchus asper*), yellow nutsedge (*Cyperus esculentus*), purple nutsedge (*Cyperus rotundus*), lupine (*Lupinus formosus*), and grasses of the family Gramineae such as annual rye grass, blue grass, water grass, barnyard grass, bermuda grass, fescue, mat grass, Johnson grass, and the like.

The compositions useful in the methods of this invention comprise a growth regulating amount of the L-(d)-lactic acid; i.e., the dextrorotatory isomer. The effectiveness of such compositions to stimulate the growth and/or fruit-bearing capability of vegetation and to inhibit the growth of or kill vegetation (depending on dosage rate) is apparently attributable to the plant growth regulant activity of the uncomplexed, monomolecular, L-(d)-isomer of lactic acid. The D-(l)-isomer of lactic acid not only does not promote vegetative growth or fruit productivity, it appears to inhibit the activity of the L-isomer to the point that the racemic mixture, i.e., the 50—50 blend of the levorotatory and dextrorotatory isomers, has only marginal growth regulant activity, if any. As is the case with all compounds which are applied to plants as solutes, the D-lactic acid does exhibit phytotoxicity if sufficient quantities of that material are applied to the plant. Such activity is very similar to that observed with very simple compounds such as sodium chloride and other soluble salts, which exhibit phytotoxicity when foliarily applied to essentially any crop. At sufficient dosage rates, such compounds will inhibit the growth of plants and will ultimately kill the treated plants.

I have also found that L-lactic anhydride and polylactides of the L-isomer (self esterification products of lactic acid) are active plant growth regulants and are as active as monomolecular L-lactic acid. All of these compounds exhibit regulant activity at very low concentrations, e.g., of about $10^{-10}$ molar and less. Lactic anhydride and higher polylactides form from monomolecular lactic acid at lactic acid concentrations of about 50 percent or greater in water. Both lactic anhydride and polylactides revert to monomolecular lactic acid upon dilution with water to concentrations below 50 percent. The active form of the growth regulant in the plants may be monomolecular L-lactic acid or polylactides of L-lactic acid of varying molecular weight. The polylactides could form on the foliage of treated vegetation (even when monomolecular lactic acid is applied in relatively dilute solutions) upon evaporation of water from the applied solution. The polylactides, if applied as such or formed on the plant foliage, probably hydrolyze within the plant (upon exposure to water) to form monomolecular lactic acid. Similarly, compounds which, in a plant environment, are converted to L-lactic acid or the anhydride or polylactides of L-lactic acid, are also effective for introducing the active growth regulant into treated plants. Whatever the active species actually is, I have found that monomolecular L-lactic acid and the anhydride and higher polylactides of L-lactic acid exhibit growth regulant activity when contacted with plants. Accordingly, when employed to describe the various aspects of this invention, the term L-lactic acid is intended to incorporate the anhydride and higher polylactides of L-lactic acid and compounds which convert to L-lactic acid or its anhydride or polylactides when applied to plants, as well as L-lactic acid itself.

One of the unexpected discoveries in the present invention is that the D-(l)-isomer exhibits little, if any, plant growth regulant activity, being at least 10 times, and probably at least 100 times, less active than the L-(d)-isomer. Further the D-isomer appears to inhibit or suppress the activity of the L-isomer. Accordingly, the preferred compositions useful in the methods of this invention comprise those in which the L-isomer constitutes at least a major portion of the lactic acid present. Usually the L-isomer will comprise at least about 60, preferably at least about 80, and most preferably at least about 90 percent of the lactic acid contained in the composition. Presently, the most preferred compositions are those in which the L-isomer constitutes 80 to 100 percent, and preferably 100 percent of the lactic acid contained in the composition as applied. Thus, the most preferred compositions are those in which the lactic acid present consists essentially of the dextrorotatory L-isomer.

The L-isomer can be applied neat although this procedure is usually undesirable for stimulating plant growth due to the high specific activity of the L-isomer. The L-isomer stimulates plant growth at concentrations as low as $10^{-10}$ molar Application of the neat material or concentrated solutions also complicates the distribution of the active component to the treated crop. Accordingly, the compositions useful in the methods of this invention usually constitute solutions of the L-isomer in a suitable solvent such as water, lower molecular weight mono- and polyhydric alcohols, ethers, carbon disulfide, and similar solvents which do not react with the L-isomer (and thereby negate its activity) under normal handling, storage and application conditions. Aqueous solutions of the L-isomer are very active growth regulants and are presently preferred. The L-isomer will usually be present in the applied solution at a concentration of at least $10^{-10}$ molar. Although L-lactic acid remains active in solution at even lower concentrations, it is difficult to apply sufficient amounts of that compound to the treated plants when using solutions of lower concentration due to run-off of the applied solution from the plant foliage. Accordingly, solutions useful in the methods of this invention will usually have L-lactic acid concentrations within the range of $10^{-10}$ to about 4 molar, normally about $10^{-9}$ to about 2 molar. Dilute solutions within these ranges are usually preferred to stimulate growth and promote fruit production. Thus, when plant stimulation is desired, the L-isomer should be present in the applied solution at a concentration within the range of about $10^{-10}$ to about $10^{-2}$ molar, generally $10^{-9}$ to about $10^{-2}$ molar, and preferably, about $10^{-7}$ to about $10^{-2}$ molar. Solutions containing higher concentrations of the active L-isomer can be conveniently employed to inhibit the growth of undesired vegetation. Concentrated solutions facilitate the application of dosage rates sufficient to inhibit plant growth as discussed hereinafter. Thus, the solutions employed to effect growth-inhibiting response will usually contain the L-isomer in concentrations of at least about $10^{-7}$ molar, generally at least about $10^{-5}$ molar, and preferably about $10^{-5}$ to about 2 molar.

I have also found that metallic salts of L-lactic acid and esters of L-lactic acid with either alcohols or acids other than L-lactic acid are less active as growth regulants than L-lactic acid itself. The salts of lactic acid can form in solutions of the L-isomer which contain significant amounts of metal cations such as calcium, nickel, cobalt, magnesium, manganese, zinc, sodium, potassium, etc. In fact, the concentration of such metal cations in many irrigation waters, such as Colorado River water, is sufficient to significantly reduce the activity of a solution of the L-isomer prepared from such waters. I have also found that compounds having active acid and/or alcohol groups can react with lactic acid to form inactive esters at pH levels below about 3 or above about 10, and that such esters also can form at pH levels within the range of about 3 to about 10, albeit at a slower rate. Thus, the activity of the L-isomer for regulating the growth of plants can be reduced or lost due to the formation of esters with other compounds containing active acid and/or alcohol groups. Compounds containing such functional groups are preferably excluded from the compositions used in the methods of this invention.

While the L-lactic acid-containing compositions described immediately above are active plant growth regulants and thus can be employed in the methods of this invention, they are hydrolytically unstable under certain conditions and are subject to bacterial attack. Bacteria can convert the active L-isomer to inactive species within a relatively short period of time at temperatures as low as 80° F. Thus, while the L-lactic acid solution can be sterilized during its manufacture, there remains a significant risk of bacterial contamination during storage, transportation, mixing, and application.

Accordingly, the novel compositions of this invention which are stabilized against hydrolytic decomposition and bacterial attack are presently preferred for use to regulate the growth of plants in accordance with the methods of this invention. These novel compositions comprise lactic acid of which a major portion is the dextrorotatory L-(d)-isomer of lactic acid and a preservative which is sufficient to prevent conversion of the L-isomer to an inactive form by bacterial attack. Suitable preservatives include sufficient acid concentrations to maintain a pH of about 5 or less and/or sterilants which inhibit bacteria growth.

The hydrolytic stability of the L-isomer can be maintained in aqueous solutions by maintaining solution pH within the range of about 3 to about 10, preferably within the range of about 4 to about 8, and most preferably within the range of about 4 to about 6. Lactic acid will react with water at relatively mild temperatures as low as 80° F. under either basic or acid conditions outside the preferred ranges. The rate of hydrolysis is relatively slow at low temperatures e.g., 80° F., and increases rapidly as temperature is increased. The rate of hydrolytic conversion of the L-isomer is also relatively low at pH levels of about 3 and about 10, and increases dramatically as pH drops below 3 or is increased to levels above 10. The rate of hydrolysis can also be reduced by reducing the water concentration in the composition, i.e., increasing the lactic acid concentration. However, the hydrolytic conversion of L-lactic acid can increase dramatically upon dilution of the concentrated acid prior to application if the solution pH is not maintained within the prescribed ranges. Accordingly, the preferred aqueous solutions of this invention contain sufficient acid and/or base to maintain the pH of the solution within the ranges described above. pH buffers are also particularly convenient for this purpose and should have buffer points within the range of about pH 3 to about pH 10, preferably about pH 4 to about pH 6. The buffers also should be nonreactive with the L-lactic acid. Suitable pH buffers include $H_3PO_4$—$xH_2PO_4$, citric acid—x-citrate (wherein x connotes a monovalent cation such as sodium, potassium, and ammonium), and other buffer pairs which have buffer points within the prescribed ranges. The salt cation contained in the buffer pair should not be present in a concentration sufficient to deactivate a significant portion of the lactic acid. For the same reason, the ammonium form of the buffer salt is presently preferred since it does not produce insoluble lactates which cause precipitation of the active component from the aqueous solution.

Essentially any acid, including lactic acid, can be employed to maintain a pH of about 5 or less in the compositions of this invention and thereby minimize the bacterial deactivation of the L-isomer. However, concentrations of lactic acid which are sufficient to maintain pH levels of about 5 or less are often above the concentration desired in the applied solution. Accordingly, the addition of other acids is presently preferred. Illustrative of suitable acids are phosphoric, sulfuric, nitric, hydochloric, and similar acids which do not form stable esters or salts with the L-isomer component.

Bacterial decomposition of the L-isomer can also be inhibited, or negated altogether by any one of various known sterilants, such as the bacteriolytic and bacteriostatic compositions. As is the case with other components of the novel compositions of this invention, the sterilant should not react with lactic acid to form stable salts or esters under normal handling conditions. Illustrative of sterilants that can be employed in the novel compositions of this invention are ethanol, formaldehyde, terramiacan, xylene, toluene, phenylmercuric nitrate, phenylmercuric acetate, copper sulfate, sodium azide, hydrogen peroxide, chlorine, benzisothiozolone, 2[(hydroxymethyl)amis]ethanol, 1-(3-chloroalkyl)-3,5,7-triaza-1-azoneaodamantane chloride, dibromocyanobutane, etc. Other stable sterilants, i.e., sterilants which do not react with lactic acid, can be identified by blending the sterilant with the desired aqueous solution of L-lactic acid and monitoring the stability of the lactic acid in the sterilant-containing solution by nuclear magnetic residence (NMR). NMR can be employed to monitor the frequency and magnitude of spectral peaks characteristic of a selected nucleus e.g., a hydrogen nucleus in the L-lactic acid molecule. Persistent spectral peak magnitude and frequency over a period of five or six hours indicate stability. Diminished magnitude or a shift in peak frequency associated with the selected hydrogen nucleus indicate stability, i.e., that the arrangement of functional groups in the lactic acid molecule has been modified. Illustrative unstable sterilants are thiophosphate esters such as melathion, parathion, etc., which should ordinarily not be employed in the compositions of this invention since they react with L-lactic acid and reduce or eliminate its activity as a growth regulant. Sterilant concentrations within the range of about 10 to about 4,000 parts per million (ppm) are usually effective for most applications.

In accordance with the methods of this invention, the plants to be regulated are contacted with a growth regulating amount of the compositions useful in this invention. The L-(d)-lactic acid-containing composition can be applied to the foliage and/or to the roots of the treated plants. The timing of application is relatively important when it is desired to increase the fruit production of fruit-bearing plants. In general, the L-lactic acid component should be applied to the plants during the flowering stage or in the early stages of the fruit-bearing cycle, or both. Ideally, the L-lactic acid component can be applied to the plants at one or more times between the first bud stage and the fruit-set stage, preferably between the first-bud stage and the petal-drop stage for both annual and perennial varieties. Significant increases, e.g., 10 percent and more, in fruit production can be achieved by treatment at essentially any time within these stages of plant development. However, it is presently preferred that at least one application of the L-lactic acid component be made within several days of the first-bud stage of development.

Significant improvements in foliage development on non-fruit bearing plants, such as grasses and timber crops, can be accomplished at any time during the growth stage, usually between the spring and fall when the crop is at its active growing cycle.

Application timing is not critical with respect to the herbicidal activity of the L-lactic acid compositions useful for the methods of this invention. Thus, such compositions can be employed to control the growth of vegetation at any time during the growth cycle. However, it is presently preferred that the undesired vegetation be treated during the early stages of its development.

Significant increases in the growth of non-fruit bearing crops and in the growth and fruit production of fruit-bearing crops can be realized by foliar application of the L-lactic acid component at dosage rates within the range of about 2 to about 100, usually about 4 to about 50, and preferably about 4 to about 25 ounces of L-lactic acid per acre. The lower dosage rate range of 4 to about 25 ounces per acre is ideally suited to most agricultural row crops and flowering nursery crops. Crops which have a larger abundance of foliage, such as wood crops and some grain and fiber crops such as wheat, corn, and cotton, benefit more by contact with higher dosages within the broader range of about 2 to about 100 ounces per acre of L-lactic acid. Significant growth stimulation can also be achieved by applying the L-lactic acid to the soil in the vicinity of the plant roots. Suitable dosage rates for this mode of application are usually within the range of about 8 to about 400 ounces per acre, preferably about 10 to about 200 ounces per acre of L-lactic acid.

The enhancement in vegetative growth and the increase in fruit production is dose-sensitive to some extent for each crop. As a rule, crops having a greater abundance of vegetative growth, such as cotton and wood crops, should be treated with higher dosage rates of L-lactic acid than are physically smaller plants such as vegetables and tuberous crops which have lesser amounts of vegetative growth.

Undesired vegetation can be eliminated by treating the foliage or soil in the vicinity of the plant roots with the L-lactic acid component at herbicidally effective dosage rates. Herbicidally effective dosage rates usually correspond to at least about 50, generally at least about 80, and preferably at least about 100 ounces per acre of L-lactic acid. Adequate control of most plants can generally be achieved at dosage rates within the range of about 80 to about 2,000, preferably about 100 to about 2,000 ounces per acre when foliarily applied.

The concentration and dosage rate of the L-lactic acid component should be correlated to provide adequate spray volume to contact a significant portion of the treated foliage and enable adequate distribution of the applied solutions as a spray with available equipment. Spray volumes in the range of about 5 to about 200 gallons per acre are sufficient to afford adequate coverage and spray distribution for essentially all plant types. Spray volumes of about 5 to about 100 gallons per acre are usually adequate for most agricultural crops, and spray volumes within the range of about 10 to about 60 gallons per acre are presently preferred for the treatment of agricultural row crops and nursery plants. As in the case of dosage rate, the optimum spray volume will vary depending upon crop type, and primarily as a function of the amount of vegetative growth presented by the treated plants. Thus, relatively higher spray volumes are better suited for the treatment of larger crops such as cotton, corn and tree crops, while lower spray volumes are better suited for the treatment of vegetables and tuberous plants. When the L-lactic acid is injected into the plant root zone, the volume of L-lactic acid solution injected per acre should be sufficient to afford adequate distribution of the L-lactic acid throughout the root zone of the treated plants. Dosage rates suitable for this purpose will usually be within the range of about 10 to about 400, generally about 20 to about 400, and preferably about 30 to about 300 gallons per acre.

The invention is further described by the following examples which are illustrative of specific modes of practicing the invention and are not intended as limiting the scope of the invention as defined by the appended claims.

EXAMPLE 1

Separate portions of pure L-(d)-lactic acid are diluted with distilled water to produce five different solutions having concentrations of $10^{-1}$, $10^{-3}$, $10^{-5}$, $10^{-7}$, and $10^{-9}$ molar. Three separate 5 ml portions of the $10^{-1}$ molar solution are then placed in three separate petri dishes lined with filter paper and each containing approximately 15 garden cress seeds. Three separate 5 ml portions of the remaining four solutions are also placed in filter paper-lined petri dishes containing approximately 15 garden cress seeds. A sixth series of three petri dishes containing approximately 15 garden cress seeds is treated only with distilled water. The garden cress seeds are germinated in the dark for three days after which each seed root in each petri dish is measured and all root lengths for each series of three replicates is averaged to obtain an average root length for that treatment. The average length of each replicate is then divided by the average length of the control (water only) to yield a root length ratio $L_{test}/L_{control}$ ($L_t/L_c$). Values below 1 indicate that the root length in the test series is less than that of the control series and that root growth suppression has occurred. Values for the $L_t/L_c$ ratio greater than 1 indicate root growth enhancement.

These results are presented graphically in FIG. 1 and indicate that the root growth suppression-stimulation promoted by a L-lactic acid solution is characteristic of classical auxin-like activity. Also illustrated graphically in FIG. 1 are data published in the literature for indole acetic acid (IAA) a widely studied plant growth regulant.

Significant root growth stimulation occurred with L-lactic acid at concentrations approximately 2 orders of magnitude below those at which similar responses were induced by indole acetic acid. Thus, L-lactic acid is a much more active plant growth regulant than is indole acetic acid, at least so far as that activity is evidenced by the cress seed root elongation test.

EXAMPLE 2

Figure 2:
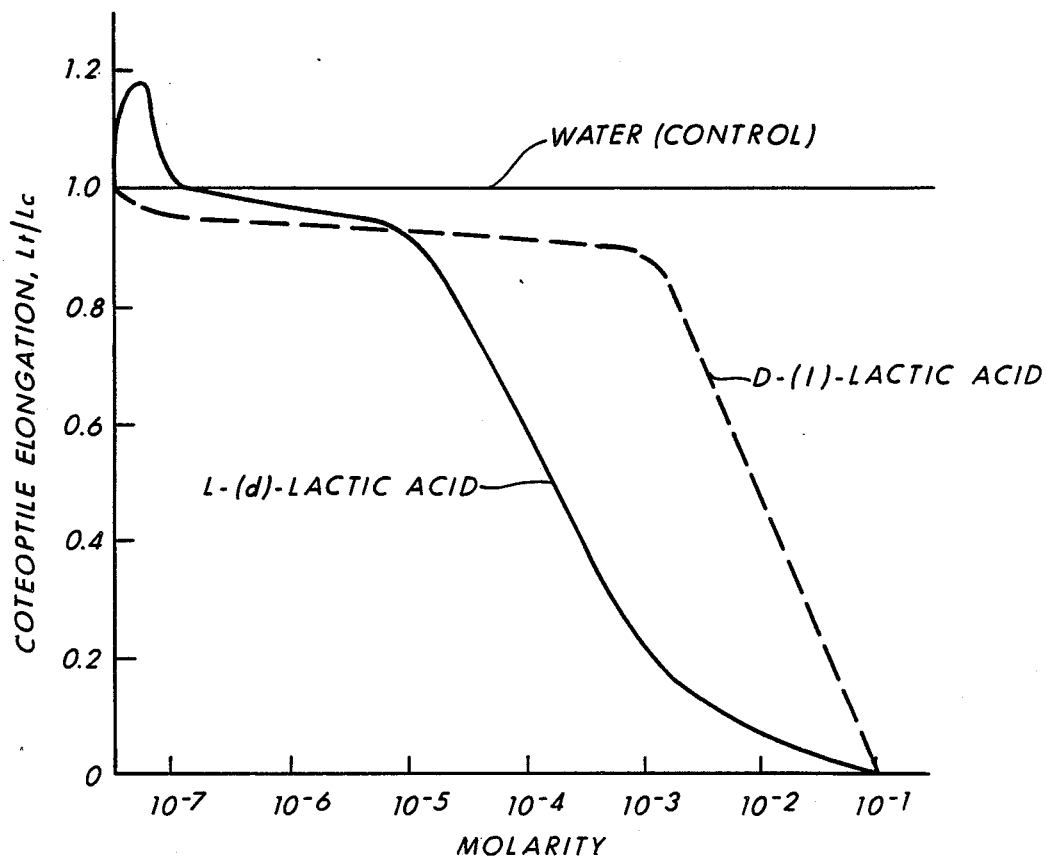
FIG. 2 is a similar graphic presentation of data illustrating the root growth regulating activity of L-lactic acid and of D-(d)-lactic acid.

The garden cress seed root elongation-suppression test described in Example 1 is repeated using three replicates each of four different concentrations of L-lactic acid in distilled water, which concentrations corresponded to $10^{-1}$, $10^{-3}$, $10^{-5}$, and $10^{-7}$ molar. Germinated seed root lengths are measured and averaged as described in Example 1. These results are presented graphically in FIG. 2. The portion of the curve in FIG. 2 which represents the response of the garden cress seed roots to L-lactic acid concentrations below $10^{-7}$ molar is reproduced based on the results of Example 1.

EXAMPLE 3

The garden cress seed root elongation-suppression test described in Example 1 is repeated employing four different concentrations of D-lactic acid (the levorotatory isomer) in distilled water. These concentrations correspond to $10^{-1}$, $10^{-3}$, $10^{-5}$, and $10^{-7}$ molar. Three separate replicates are tested at each concentration and root lengths are measured and averaged as described in Example 1. The results are presented graphically in FIG. 2. Comparison of the results of Examples 2 and 3 illustrates that the levorotatory [D-(1)-] isomer of lactic acid has little if any growth regulating activity and that it is a far less active plant growth regulant than is the levorotatory isomer. The results of Example 3 also indicate that the D-lactic acid has little, if any, tendency to stimulate the growth of germinating seed roots even at relatively low concentrations.

EXAMPLE 4

Yellow flowering variety alfalfa seeds are planted in a sandy loam soil after which 20 ml of a $10^{-5}$ molar solution of L-lactic acid are applied topically to the soil. Four replicates are treated and these are compared to four replicates of the same seed population planted in the same soil but not treated with the L-lactic acid solution. More seeds germinate in the treated plots than in the untreated (control) plots. All plants are harvested after nine weeks of growth and weighed. The alfalfa treated with L-lactic acid produces 25 weight percent more vegetative growth than does the untreated control.

EXAMPLE 5

The operation of Example 4 is repeated with the exception that 50 ml of the $10^{-5}$ molar L-lactic acid solution is applied to the soil surface after planting of the yellow flowering variety alfalfa seeds. Again more plants survive in the treated plots and the treated plants produce approximately 25 percent more vegetation growth than the control.

EXAMPLE 6

Approximately equal numbers of yellow flowering variety alfalfa seeds are planted in several pots containing a sandy loam soil. Four series of four pots each are treated with 20 ml of a $10^{-5}$ molar solution of L-lactic acid in distilled water. The solution is applied to the plants by foliar spraying at emergence (5 days after planting), and three weeks, six weeks, and nine weeks after emergence. The plants are harvested twelve weeks after emergence, weighed, and compared to an untreated control. The test series which are treated five days after planting and three weeks and six weeks after emergence all produce approximately 20 to 25 weight percent more vegetative growth than do the control series. The plants treated nine weeks after emergence do not produce an amount of vegetative growth above that produced by the untreated control plants, which could be defined as statistically significant.

EXAMPLE 7

The operation of Example 6 is repeated with the exception that 50 ml of the $10^{-5}$ molar L-lactic acid solution is applied to each test series. As in the case of the 20 ml treatments, the plants treated 5 days after planting, and two weeks and six weeks after emergence show approximately 20 to 25 weight percent greater vegetative growth than the control, while the plants treated nine weeks after emergence and harvested twelve weeks after emergence do not evidence a significant gain in vegetative growth over the control. The absence of a statistically significant gain in vegetative growth for the nine week treatment may be due to the relatively short time between treatment and harvest.

EXAMPLE 8

Tiny Tim tomatoes which have already set fruit which is approximately 0.5 to 1.5 centimeters in diameter are treated with an aqueous solution of L-lactic acid in distilled water having a lactic acid concentration of $10^{-5}$ molar. The solution is applied to the plant foliage at a rate of approximately 4 ml per plant. No significant increase in fruit size or quantity is obtained in comparision to untreated control plants.

EXAMPLE 9

The operation of Example 8 is repeated with the exception that the L-lactic acid solution foliarily applied to the Tiny Tim tomato plants has a lactic acid concentration of $10^{-3}$ molar. Again no increase in fruit size or quantity is observed as compared to the untreated controls.

EXAMPLE 10

The operation of Example 8 is repeated with the exception that the tomato plants are treated with two separate foliar applications of approximately 4 ml each of the $10^{-3}$ molar L-lactic acid solution in distilled water. The first application is made at the full-bloom stage (maximum flowering) and the second application is made two weeks later (after fruit set). The tomatoes are harvested after reaching maturity and the treated tomatoes are approximately 15 percent larger and mature approximately 50 percent faster than do tomatoes on the untreated control plants.

EXAMPLE 11

The operation of Example 10 is repeated with the exception that the L-lactic acid solution applied to the tomato plants has an L-lactic acid concentration of $10^{-5}$ molar. As in the case of the $10^{-3}$ molar solution, the treated plants yield tomatoes which are approximately 15 percent larger by weight and which mature approximately 50 percent faster than the untreated controls.

EXAMPLE 12

Navel orange trees are treated by foliar application at the first petal-drop stage of five ounces per acre of L-lactic acid in 30 gallons per acre aqueous spray volume. The crop is allowed to set and mature and is harvested and weighed. The untreated control plot produces 820 boxes of navel oranges per acre while the treated plot produces 1,218 boxes of the oranges per acre.

EXAMPLE 13

Cabernet grapes are treated by foliar application of L-lactic acid at a dosage rate corresponding to 8 ounces of L-lactic acid per acre dissolved in 30 gallons per acre spray volume. The foliar application is made at the first berry stage and the grapes are allowed to mature and are harvested. The yield from the treated grape plants is 15 to 20 percent greater than that of untreated control plants in the same population and the sugar content of the treated grapes is approximately 2 percentage points higher than is the sugar content of the untreated grapes.

EXAMPLE 14

Sylvaner Riesling grapes are treated by foliar application of L-lactic acid at a rate corresponding to 8 ounces per acre in 30 gallons per acre of spray volume at the first berry stage. The grapes are allowed to mature and are harvested and compared to grapes produced by untreated control plants in the same population. The yield from the treated Riesling grape plants is 15 to 20 percent greater than that of the untreated controls.

EXAMPLE 15

Murietta tomatoes are treated by foliar application of a solution of L-lactic acid at a dosage rate corresponding to 8 ounces of L-lactic acid per acre dissolved in 30 gallons per acre spray volume. The application is made at peak flowering and the fruit is allowed to set and mature and is harvested and compared to fruit obtained from untreated plants in the same population. The yield of the treated plants is approximately 30 percent higher than that of the untreated plants.

EXAMPLE 16

Pima cotton is treated by foliar application of an aqueous L-lactic acid solution at a dosage rate corresponding to 16 ounces of L-lactic acid per acre dispersed in 30 gallons per acre of spray volume. The application is made at peak flowering and the cotton is allowed to mature and is harvested and compared to cotton obtained from untreated, control plants in the same population. The treated plants yield approximately 20 percent more cotton than the untreated plants.

EXAMPLE 17

Valencia oranges are treated by foliar application of 16 ounces per acre of L-lactic acid in 30 gallons per acre of aqueous solution spray. The spray is applied at the first petal-fall stage (peak flowering), and the fruit is allowed to mature and is harvested under normal horticultural conditions. The treated trees produce 1,400 boxes per acre of Valencia oranges as compared to 800 boxes per acre for untreated control trees in the same population.

EXAMPLE 18

Zinfandel grapes are treated by foliar application of 4 ounces per acre of L-lactic acid in 30 gallons per acre of aqueous solution spray volume. The spray is applied at the first berry stage, and the grapes are allowed to mature and are harvested under normal horticultural conditions. The yield of the treated Zinfandel grape plants is 12 percent higher than that of untreated plants in the same population.

EXAMPLE 19

Barley plants, approximately 12 inches high, are treated with L-lactic acid by foliar application of sufficient aqueous solution containing 25 weight percent L-lactic acid to cover the plant foliage. Control plants were foliarly contacted with an equal quantity of distilled water. Severe damage results to the L-lactic acid-treated plants within two hours of application. Some minor revegetation occurs within two weeks. There is no damage to the control plants which are treated only with water.

EXAMPLE 20

The operation of Example 19 is repeated with the exception that the applied solution contains 6 weight percent L-lactic acid. Some foliar damage is apparent within 2 hours of application. All plants recover in approximately two weeks.

EXAMPLE 21

Mature, Tiny Tim tomato plants are treated by foliar application of sufficient aqueous solution containing 25 weight percent L-lactic acid to cover the plant foliage. Control plants of the same population are foliarly treated with water only. Severe foliage damage is apparent within 2 hours and all treated plants ultimately die. There is no damage to the control plants.

EXAMPLE 22

The operation of Example 21 was repeated with the exception that the foliage of the tomato plants is contacted with an aqueous solution containing 6 weight percent lactic acid. Again, severe damage is apparent within 2 hours and results in the complete mortality of the treated plants. There is no damage to control plants which are foliarly treated only with distilled water.

While particular embodiments of the invention have been described, it will be understood, of course, that the invention is not limited thereto since many obvious modifications can be made and it is intended to include within this invention any such modifications as will fall within the scope of the appended claims.

Having described my invention, I claim:

1. A method for stimulating the productivity of plants which comprises contacting said plants with a productivity stimulating amount of a composition which comprises lactic acid, and wherein the L-d(d)-isomer of lactic acid constitutes at least a major portion of said lactic acid.

2. The method defined in claim 1 wherein said L-(d)-isomer of lactic acid is present in said composition in the form of a member selected from the group consisting of monomolecular lactic acid, lactic anhydride, polylactides of lactic acid, and combinations thereof.

3. The method defined in claim 1 wherein said composition further comprises a nonreactive preservative selected from the group consisting of (a) sufficient acid other than said lactic acid to maintain a pH in said composition of about 5 or less, (b) a sterilant, and (c) combinations thereof.

4. The method defined in claim 1 wherein said composition has a pH within the range of about 3 to about 10 sufficient to maintain the hydrolytic stability of said L-(d)-isomer of lactic acid.

5. The method defined in claim 1 wherein said composition has a pH within the range of about 4 to about 6 sufficient to maintain the hydrolytic stability of said L-(d)-isomer of lactic acid.

6. The method defined in claim 4 wherein said composition further comprises a pH buffer having a buffering point within the range of about pH 3 to about pH 10.

7. The method defined in claim 5 wherein said composition further comprises a pH buffer selected from the group consisting of phosphoric acid x-dihydrogen phosphate, citric acid x-citrate, and combinations thereof, wherein x is a monovalent cation other than hydrogen.

8. The method defined in claim 1 wherein said L-(d)-isomer of lactic acid constitutes at least about 60 percent of the lactic acid contained in said composition.

9. The method defined in claim 1 wherein said L-(d)-isomer of lactic acid constitutes about 80 to 100 percent of said lactic acid, and said composition has a pH within the range of about 3 to about 8 and further comprises a pH buffer having a buffer point within the range of about pH 3 to about pH 8, and a sterilant, which sterilant is sufficient to inhibit the bacterial decomposition of said L-(d)-isomer of lactic acid.

10. The method defined in claim 1 wherein said composition comprises an aqueous solution of said L-(d)-isomer of lactic acid in which the combination of said L-(d)-isomer is within the range of about $10^{-10}$ to about $10^{-2}$ molar.

11. The method defined in claim 1 wherein said composition is applied to the plants at a dosage rate corresponding to about 2 to about 100 ounces of said L-(d)-isomer of lactic acid per acre.

12. The method defined in claim 1 wherein said composition is applied to said plants at a dosage rate corresponding to about 4 to about 50 ounces of said L-(d)-isomer of lactic acid per acre.

13. The method defined in claim 1 wherein said composition is applied to said plants at a dosage rate corresponding to about 4 to about 25 ounces of said L-(d)-isomer of lactic acid per acre.

14. The method defined in claim 1 wherein said composition is applied to a member selected from the group consisting of the foliage of said plants, the ground in the vicinity of the roots of said plants, and combinations thereof, at a dosage rate corresponding to at least about 2 ounces of said L-lactic acid per acre, and said L-(d)-isomer constitutes about 80 to about 100 percent of said lactic acid.

15. The method defined in claim 14 wherein said composition is applied to the foliage of said plants.

16. The method defined in claim 14 wherein said composition is applied to the ground in the vicinity of the root zone of said plants, either before or after the emergence of said plants, and said plants are selected from nonfruiting grasses.

17. The method defined in claim 15 wherein said plants are selected from the fruit-bearing plants, and said composition is foliarily applied to said fruit-bearing plants during the fruit-bearing cycle of said plants.

18. The method defined in claim 17 wherein said plants are selected from grains, vegetables, tubers, and fruiting plants, and said composition is foliarily applied to said plants at a time between about the first bud stage and the fruit-set stage of said fruit bearing cycle of said plants.

19. The method defined in claim 17 wherein said composition is applied to said plants at a dosage rate corresponding to about 2 to about 100 ounces of said L-(d)-isomer of lactic acid per acre.

20. The method defined in claim 1 wherein said lactic acid consists essentially of said L-isomer.

21. The method defined in claim 20 wherein the concentration of said L-lactic acid in said composition corresponds to about $10^{-10}$ to about $10^{-2}$ molar.

22. The method defined in claim 1 wherein said plants are selected from the group consisting of vegetables, grains, fiber crops, tuberous crops, timber crops, grasses, ornamental flowering plants, and fruiting plants.

23. A method for stimulating the productivity of plants which comprises contacting said plants with a productivity stimulating amount of a composition which comprises lactic acid, wherein the dextrorotatory L-isomer of lactic acid constitutes about 80 to about 100 percent of said lactic acid.

24. The method defined in claim 23 wherein said lactic acid consists essentially of said L-isomer of lactic acid.

25. The method defined in claim 23 wherein said lactic acid consists essentially of the L-isomer of lactic acid, and said composition further comprises a preservative selected from the group consisting of (a) sufficient acid to maintain a pH in said composition of about 5 or less, (b) a sterilant sufficient to inhibit bacterial decomposition of said lactic acid, and (c) combinations thereof.

26. A method for stimulating the productivity of plants, which method comprises contacting said plants with a productivity stimulating amount of a composition which comprises lactic acid, wherein said lactic acid consists essentially of the L-isomer of lactic acid.

27. A method for stimulating the productivity of plants selected from the group consisting of vegetables, fruits, nuts, grains, grasses, fiber crops, wood crops, flowering plants, and combinations thereof, which method comprises foliarly applying to said plants, during the bearing cycle of said plants, a composition comprising lactic acid in which composition the L-(d)-isomer of lactic acid constitutes about 80 to 100 percent of said lactic acid, and wherein said composition is applied to said plants at a productivity stimulating dosage rate corresponding to at least about 2 ounces per acre of said L-(d)-isomer of lactic acid.

28. The method defined in claim 27 wherein said plants are selected from the group consisting of grains, grasses, fiber crops, fruiting plants, and combinations thereof, said lactic acid consists essentially of said L-isomer of lactic acid, and said composition is applied to said plants at a period between the first-bud stage and the fruit-set stage of said plants.

29. The method defined in claim 28 wherein said plants are selected from citrus, tomatoes, berry crops and cotton.

30. The method defined in claim 27 wherein said lactic acid consists essentially of the L-isomer of lactic acid, and said composition further comprises a preservative sufficient to prevent the bacterial decomposition of said lactic acid.

31. The method defined in claim 27 wherein said L-(d)-isomer of lactic acid is present in said composition at a concentration within the range of about $10^{-10}$ to about $10^{-2}$ molar, and said composition is applied to the foliage of said plants at a dosage rate corresponding to about 2 to about 100 ounces of said L-(d)-isomer of lactic acid per acre.

32. A method for stimulating the growth of plants selected from the group consisting of vegetables, grains, tuberous crops, timber crops, grasses, ornamental flowering plants, and fruiting plants, which method comprises contacting said plants with a growth-stimulating amount of lactic acid, wherein the L-isomer of lactic acid constitutes at least a major portion of said lactic acid.

33. The method defined in claim 1 wherein said L-(d)-isomer constitutes about 80 to 100 percent of said lactic acid.

* * * * *